(12) United States Patent
Mehta et al.

(10) Patent No.: US 10,825,111 B2
(45) Date of Patent: *Nov. 3, 2020

(54) VERIFIED SOCIAL MEDIA CONTENT

(71) Applicant: McAfee, LLC, Santa Clara, CA (US)

(72) Inventors: Kunal Mehta, Hillsboro, OR (US);
Carl D. Woodward, Santa Clara, CA (US); Steven Grobman, El Dorado Hills, CA (US); Ryan Durand, Hillsboro, OR (US); Simon Hunt, Naples, FL (US)

(73) Assignee: McAfee, LLC, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/236,087

(22) Filed: Dec. 28, 2018

(65) Prior Publication Data
US 2019/0139156 A1    May 9, 2019

Related U.S. Application Data

(63) Continuation of application No. 14/976,397, filed on Dec. 21, 2015, now Pat. No. 10,204,384.

(51) Int. Cl.
*H04L 29/00* (2006.01)
*G06Q 50/00* (2012.01)
(Continued)

(52) U.S. Cl.
CPC .............. *G06Q 50/01* (2013.01); *A61B 5/117* (2013.01); *A61B 5/165* (2013.01); *A61B 5/4845* (2013.01);
(Continued)

(58) Field of Classification Search
CPC ........ G06F 21/62; G06F 21/316; G06F 21/53; G06F 21/552; G06Q 10/06395;
(Continued)

(56) References Cited

U.S. PATENT DOCUMENTS 5,987,610 A    11/1999  Franczek et al.
6,073,142 A     6/2000  Geiger et al.
(Continued)

FOREIGN PATENT DOCUMENTS

WO    2017112137 A1    6/2017

OTHER PUBLICATIONS

Final Office Action issued in U.S. Appl. No. 14/976,397 dated Jun. 19, 2018, 22 pages.
(Continued)

*Primary Examiner* — Don G Zhao
(74) *Attorney, Agent, or Firm* — Patent Capital Group

(57) ABSTRACT

There is disclosed in one example a social media server, including: a processor; a trusted input/output (IO) interface to communicatively couple to a consumer device; a network interface to communicatively couple to an enterprise; and a memory having stored thereon executable instructions to instruct the processor to provide a data loss prevention (DLP) engine to: receive via the trusted IO interface a signed and encrypted user posting for the social media service, the user posting including a signed user state report verifying that the user has passed a biometric screening; transmit content of the user posting to the enterprise via the network interface for DLP analysis; receive from the enterprise a notification that the user posting has passed DLP analysis; and accept the user posting.

20 Claims, 10 Drawing Sheets

(51) Int. Cl.
*G06Q 10/06* (2012.01)
*G06F 21/31* (2013.01)
*G06F 21/55* (2013.01)
*H04L 29/06* (2006.01)
*A61B 5/00* (2006.01)
*A61B 5/117* (2016.01)
*A61B 5/16* (2006.01)
*H04W 12/06* (2009.01)
*H04L 29/08* (2006.01)
*G06F 21/53* (2013.01)

(52) U.S. Cl.
CPC .......... *A61B 5/6898* (2013.01); *G06F 21/316* (2013.01); *G06F 21/552* (2013.01); *G06Q 10/06395* (2013.01); *H04L 63/0861* (2013.01); *H04W 12/0609* (2019.01); *G06F 21/53* (2013.01); *G06F 2221/2133* (2013.01); *H04L 67/10* (2013.01)

(58) Field of Classification Search
CPC ..... G06Q 50/01; H04L 67/10; H04L 63/0861; A61B 5/4845; A61B 5/165; A61B 5/6898; A61B 5/117; H04W 12/06
See application file for complete search history.

(56) References Cited

U.S. PATENT DOCUMENTS

| | | | |
|---|---|---|---|
| 6,460,050 | B1 | 10/2002 | Pace et al. |
| 7,506,155 | B1 | 3/2009 | Stewart et al. |
| 9,189,599 | B2* | 11/2015 | Adler .................... G16H 50/30 |
| 9,262,517 | B2* | 2/2016 | Feng ...................... G06Q 30/02 |
| 9,378,065 | B2* | 6/2016 | Shear .................... G06F 9/5072 |
| 9,652,992 | B2 | 5/2017 | Kaleal |
| 9,792,160 | B2* | 10/2017 | Shear .................... G06F 9/5072 |
| 9,792,329 | B1* | 10/2017 | Cronin ............. G06F 16/24575 |
| 9,997,082 | B2 | 6/2018 | Kaleal |
| 2007/0173733 | A1 | 7/2007 | Le et al. |
| 2008/0033303 | A1 | 2/2008 | Wariar et al. |
| 2011/0209194 | A1* | 8/2011 | Kennedy ................ G06F 21/55 726/1 |
| 2012/0223823 | A1 | 9/2012 | Dunko |
| 2013/0013685 | A1* | 1/2013 | Moses .................... G06Q 50/01 709/204 |
| 2014/0107894 | A1 | 4/2014 | Obradovich |
| 2014/0114899 | A1* | 4/2014 | Wan ......................... G06N 5/04 706/47 |
| 2014/0195815 | A1 | 7/2014 | Taveau et al. |
| 2014/0223462 | A1 | 8/2014 | Aimone et al. |
| 2014/0258161 | A1* | 9/2014 | Brown ............... G06Q 10/1053 705/321 |
| 2014/0344205 | A1* | 11/2014 | Luna ...................... G06N 5/025 706/47 |
| 2014/0347181 | A1* | 11/2014 | Luna ................. H04M 1/72569 340/539.22 |
| 2014/0365849 | A1* | 12/2014 | Ishmael .................. H04L 51/32 715/202 |
| 2015/0020151 | A1* | 1/2015 | Ramanathan ....... G06F 21/6218 726/1 |
| 2015/0140527 | A1* | 5/2015 | Gilad-Barach ......... A61B 5/165 434/236 |
| 2016/0072903 | A1* | 3/2016 | Chakra ............... G06F 17/2785 704/9 |
| 2016/0110429 | A1* | 4/2016 | Feng ...................... G06Q 30/02 707/776 |
| 2016/0140320 | A1* | 5/2016 | Moturu ............... G06F 19/3481 434/236 |
| 2016/0151704 | A1* | 6/2016 | Wu ........................ G06Q 50/01 463/31 |
| 2016/0173435 | A1* | 6/2016 | Abou Mahmoud .... H04L 51/32 709/206 |
| 2017/0032021 | A1* | 2/2017 | Watanachote .......... H04L 51/32 |
| 2017/0032470 | A1* | 2/2017 | Watanachote ......... G06Q 50/01 |
| 2017/0039204 | A1* | 2/2017 | Blanchflower ........ G06Q 10/10 |
| 2017/0177884 | A1 | 6/2017 | Mehta et al. |
| 2019/0139155 | A1 | 5/2019 | Mehta et al. |

OTHER PUBLICATIONS

International Search Report and Written Opinion issued in PCT Application No. PCT/US2016/062160 dated Feb. 17, 2017; 14 pages.

Non-Final Office Action issued in U.S. Appl. No. 14/976,397 dated Nov. 30, 2017, 32 pages.

* cited by examiner

VERIFIED SOCIAL MEDIA CONTENT

CROSS REFERENCE TO RELATED APPLICATIONS

This Application is a continuation of U.S. application Ser. No. 14/976,397, filed Dec. 21, 2015, entitled "VERIFIED SOCIAL MEDIA CONTENT." The disclosure of this prior application is considered part of (and is incorporated by reference) in the disclosure of this application.

FIELD OF THE SPECIFICATION

This disclosure relates in general to the field of network security, and more particularly, though not exclusively to, a system and method for verifying social media content.

BACKGROUND

In contemporary social media platforms, such as Facebook, Instagram, Tumblr, or Snapchat, and many others, users have the ability to instantly post their thoughts in a stream-of-conscience fashion. Users can also post photographs, documents, and links very easily. This ease of use can make for a rich, entertaining social media experience.

BRIEF DESCRIPTION OF THE DRAWINGS

The present disclosure is best understood from the following detailed description when read with the accompanying figures. It is emphasized that, in accordance with the standard practice in the industry, various features are not necessarily drawn to scale, and are used for illustration purposes only. Where a scale is shown, explicitly or implicitly, it provides only one illustrative example. In other embodiments, the dimensions of the various features may be arbitrarily increased or reduced for clarity of discussion.

SUMMARY

Figure 1:
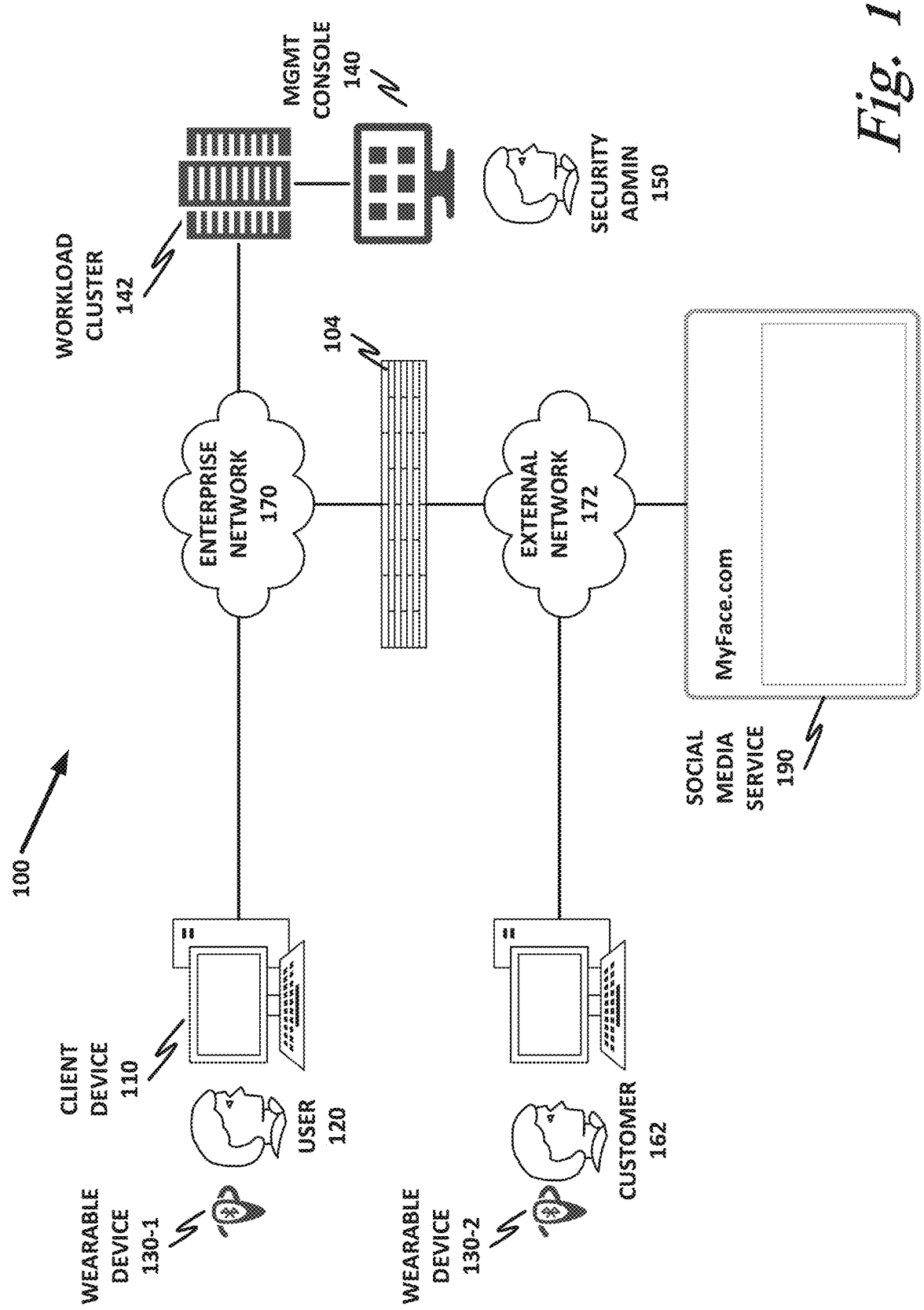
FIG. 1 is a block diagram of a social network according to one or more examples of the present specification.

In an example, there is disclosed a social media server, comprising: a processor; a trusted input/output (IO) interface to communicatively couple to a consumer device; a network interface to communicatively couple to an enterprise; and a memory having stored thereon executable instructions to instruct the processor to provide a data loss prevention (DLP) engine to: receive via the trusted IO interface a signed and encrypted user posting for the social media service, the user posting including a signed user state report verifying that the user has passed a biometric screening; transmit content of the user posting to the enterprise via the network interface for DLP analysis; receive from the enterprise a notification that the user posting has passed DLP analysis; and accept the user posting.

EMBODIMENTS OF THE DISCLOSURE

The following disclosure provides many different embodiments, or examples, for implementing different features of the present disclosure. Specific examples of components and arrangements are described below to simplify the present disclosure. These are, of course, merely examples and are not intended to be limiting. Further, the present disclosure may repeat reference numerals and/or letters in the various examples. This repetition is for the purpose of simplicity and clarity and does not in itself dictate a relationship between the various embodiments and/or configurations discussed. Different embodiments may have different advantages, and no particular advantage is necessarily required of any embodiment.

As network users' personal lives increasingly crossover with their work lives, data loss prevention (DLP) is a serious concern for any enterprise. A user who is angry, intoxicated, over-stimulated, depressed, anxious, frightened, aroused, under duress, or whose judgment is otherwise compromised may make ill-advised posts, for example to a social media platform. In contemporary social media platforms, such as Facebook, Instagram, Tumblr, or Snapchat, users have the ability to instantly post their thoughts in a stream-of-conscience fashion with very little forethought. Users can also post photographs, documents, and links very easily. While this ease of use can make for a rich, entertaining social media experience, it can be problematic for an enterprise. Other user actions may be similarly compromised by an unfit psychological state. For example, an angry user who has just had an altercation with his boss or just received a termination notice (fired or laid off) may, in the heat of the moment, access files and send them to an adverse organization, something he may not do with a level head. In a classic spy example, a user with access to secret data could encounter a sensual enemy agent, and while engaged in unauthorized activities, with impaired judgment, compromise those secret data.

Even a social media user in full possession of his or her faculties may sometimes make ill-advised or poorly-thought-out posts. In some cases, careers have been harmed and reputations compromised by a person's post without proper regard for potential consequences. Job applicants have been passed over because of old photographs showing poor judgment. Celebrities have been caught in racist or bigoted rants. Companies have fired executives who have said or done things that can damage the reputation of the company by association.

Thus, it is advantageous to provide a system and method to ensure that social media messages are sent by authorized users, and sent only when those users are in a fit mental or psychological state to post. It is also advantageous to ensure that the users are posting appropriate content, excluding for example malicious or hateful content, proprietary corporate data, government classified data, personally-identifying information, insider trading, content or statements against policy, personal opinions put forth as official corporate policy or without appropriate disclaimers, or other inappropriate content.

The system may also detect, notify, and challenge the user in case some unauthorized or untrusted post appears on their social media account.

In an example, the user operates a client device with a trusted execution environment (TEE) and protected audio-video path (PAVP) or other trusted I/O. The user may also have a wearable device with appropriate biometric data for constructing a biometric profile, which may serve as a proxy for or means for inferring the user's psychological state.

When the user attempts to post to a social media site, he may need to first authenticate to the device. Once authenticated, he may also need to pass a biometric profile to ensure that he is mentally sound to post. If the user fails the initial biometric profile, a second-tier verification may be provided, such as a cognitive ability test that is relatively easy for a sober person, but relatively difficult for a person who is compromised by alcohol, drugs, excitation, nervousness, anger, or some other factor that affects the user's cognitive ability. This verification may be provided by a combination of a verification engine on the user's own machine, and a data loss prevention (DLP) engine on an intermediate DLP server, or any suitable combination of the two.

Advantageously, a completely secure and attested path may be provided all the way from the wearable device, to the client device, to the DLP server, to the social media server.

A system and method for verified social media content will now be described with more particular reference to the attached FIGURES. It should be noted that throughout the FIGURES, certain reference numerals may be repeated to indicate that a particular device or block is wholly or substantially consistent across the FIGURES. This is not, however, intended to imply any particular relationship between the various embodiments disclosed. In certain examples, a genus of elements may be referred to by a particular reference numeral ("widget 10"), while individual species or examples of the genus may be referred to by a hyphenated numeral ("first specific widget 10-1" and "second specific widget 10-2").

FIG. 1 is a network-level diagram of enterprise 100 according to one or more examples of the present specification. In this example, enterprise 100 may be configured to provide services or data to one or more customers 162, who may access information or services via external network 172. This may require secured enterprise 100 to at least partly expose certain services and networks to the outside world, thus creating a logical security aperture.

Within secured enterprise, one or more users 120 operate one or more client devices 110. Each device may include an appropriate operating system, such as Microsoft Windows, Linux, Android, Mac OSX, Apple iOS, Unix, or similar. Some of the foregoing may be more often used on one type of device than another. For example, desktop computers or engineering workstation may be more likely to use one of Microsoft Windows, Linux, Unix, or Mac OSX. Laptop computers, which are usually a portable off-the-shelf device with fewer customization options, may be more likely to run Microsoft Windows or Mac OSX. Mobile devices may be more likely to run Android or iOS. However, these examples are not intended to be limiting.

Client devices 110 may be communicatively coupled to one another and to other network resources via enterprise network 170. Enterprise network 170 may be any suitable network or combination of one or more networks operating on one or more suitable networking protocols, including for example, a local area network, an intranet, a virtual network, a wide area network, a wireless network, a cellular network, or the Internet (optionally accessed via a proxy, virtual machine, or other similar security mechanism) by way of nonlimiting example. Enterprise network 170 may also include one or more servers, firewalls, routers, switches, security appliances, antivirus servers, or other useful network devices, which in an example may be virtualized within workload cluster 142. In this illustration, enterprise network 170 is shown as a single network for simplicity, but in some embodiments, enterprise network 170 may include a large number of networks, such as one or more enterprise intranets connected to the internet. Enterprise network 170 may also provide access to an external network, such as the Internet, via external network 172. External network 172 may similarly be any suitable type of network.

A workload cluster 142 may be provided, for example as a virtual cluster running in a hypervisor on a plurality of rack-mounted blade servers, or as a cluster of physical servers. Workload cluster 142 may provide one or more server functions, or one or more "microclouds" in one or more hypervisors. For example, a virtualization environment such as vCenter may provide the ability to define a plurality of "tenants," with each tenant being functionally separate from each other tenant, and each tenant operating as a single-purpose microcloud. Each microcloud may serve a distinctive function, and may include a plurality of virtual machines (VMs) of many different flavors, including agentful and agentless VMs. In some embodiments, a DLP server 400 (see FIG. 4) may be provisioned within workload cluster 142.

It should also be noted that some functionality of endpoint devices 110 may also be provided via workload cluster 142. For example, one microcloud may provide a remote desktop hypervisor such as a Citrix workspace, which allows users 120 operating endpoints 110 to remotely login to a remote enterprise desktop and access enterprise applications, workspaces, and data. In that case, endpoint 110 could be a "thin client" such as a Google Chromebook, running only a stripped-down operating system, and still provide user 120 useful access to enterprise resources.

One or more computing devices configured as a management console 140 may also operate on enterprise network 170. Management console 140 may provide a user interface for a security administrator 150 to define enterprise security policies, which management console 140 may enforce on enterprise network 170 and across client devices 110 and workload cluster 142. In an example, management console 140 may run a server-class operating system, such as Linux, Unix, or Windows Server. In other case, management console 140 may be provided as a web interface, on a desktop-class machine, or via a VM provisioned within workload cluster 142.

Secured enterprise 100 may communicate across enterprise boundary 104 with external network 172. Enterprise boundary 104 may represent a physical, logical, or other boundary. External network 172 may include, for example, websites, servers, network protocols, and other network-based services. In one example, a social media service 190 is available via external network 172.

In another example, secured enterprise 100 may simply be a family, with parents assuming the role of security administrator 150. The parents may wish to protect their children from undesirable content, such as pornography, adware, spyware, age-inappropriate content, advocacy for certain political, religious, or social movements, or forums for discussing illegal or dangerous activities, by way of non-limiting example. In this case, the parent may perform some or all of the duties of security administrator 150.

In any of the foregoing examples, enterprise user 120 and customer 162 may wish to interact with social media service 190. However, the enterprise to which these users belong may have concerns, as discussed above, with unrestricted access to social media service 190. Thus, users may be provided with a wearable device 130, which may be configured to provide biometric or other sensors. Data from these sensors may serve as a proxy for or a means to infer the user's psychological state or condition. Thus, a verification engine 234 (FIG. 2) operating on client device 110, or a DLP engine 434 (FIG. 4) operating on a service node in workload cluster 142, or any other suitable device, may monitor inputs from wearable devices 130, and may restrict access to social media service 190 if the user's state appears to be unsuitable.

Figure 2:
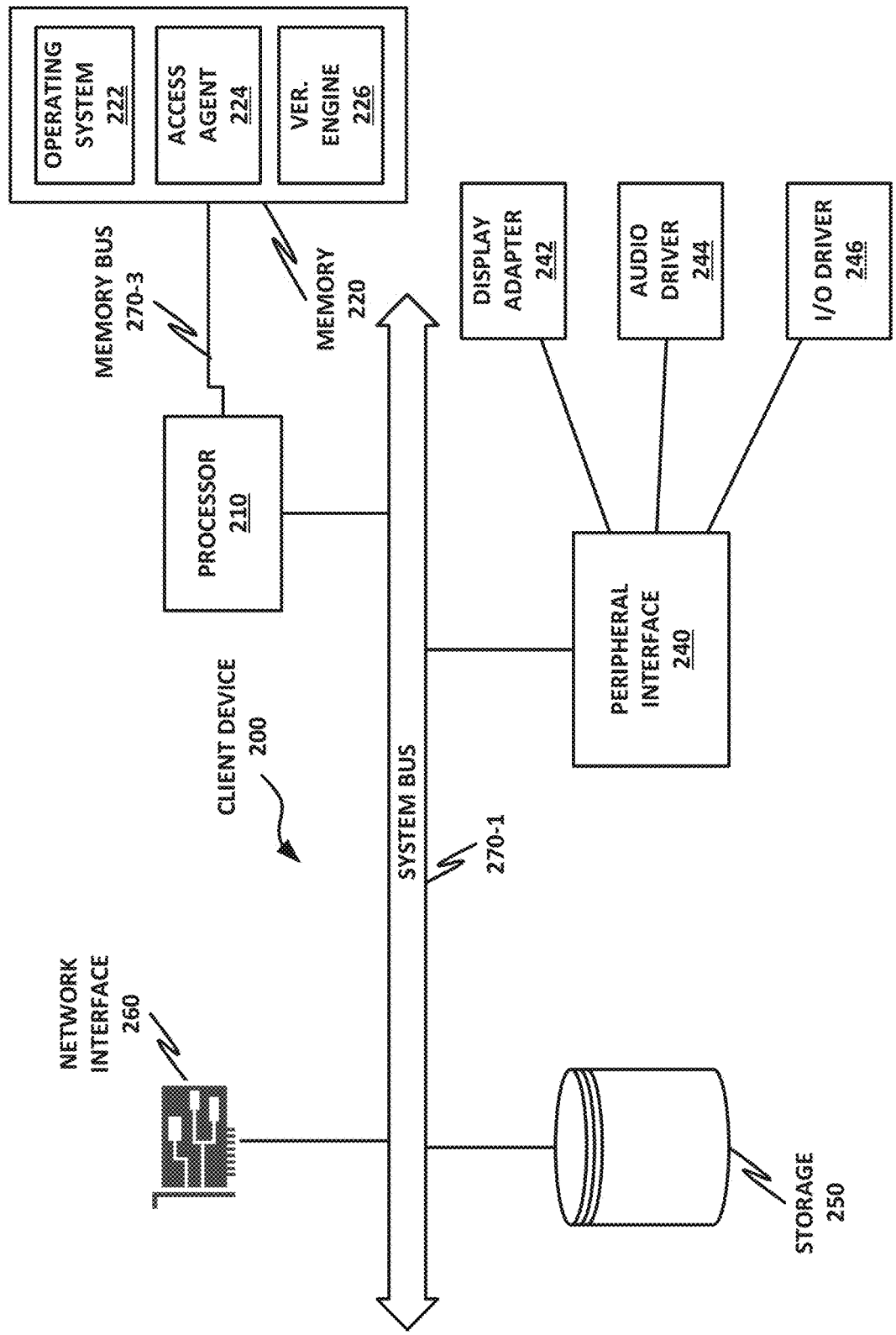
FIG. 2 is a block diagram of a client device according to one or more examples of the present specification.

FIG. 2 is a block diagram of client device 200 according to one or more examples of the present specification. Client device 200 may be any suitable computing device. In various embodiments, a "computing device" may be or comprise, by way of non-limiting example, a computer, workstation, server, mainframe, virtual machine (whether emulated or on a "bare-metal" hypervisor), embedded computer, embedded controller, embedded sensor, personal digital assistant, laptop computer, cellular telephone, IP telephone, smart phone, tablet computer, convertible tablet computer, computing appliance, network appliance, receiver, wearable computer, handheld calculator, or any other electronic, microelectronic, or microelectromechanical device for processing and communicating data. Any computing device may be designated as a host on the network. Each computing device may refer to itself as a "local host," while any computing device external to it may be designated as a "remote host."

In certain embodiments, client devices 110 may all be examples of client devices 200.

Client device 200 includes a processor 210 connected to a memory 220, having stored therein executable instructions for providing an operating system 222 and at least software portions of a verification engine 224. Other components of client device 200 include a storage 250, network interface 260, and peripheral interface 240. This architecture is provided by way of example only, and is intended to be non-exclusive and non-limiting. Furthermore, the various parts disclosed are intended to be logical divisions only, and need not necessarily represent physically separate hardware and/or software components. Certain computing devices provide main memory 220 and storage 250, for example, in a single physical memory device, and in other cases, memory 220 and/or storage 250 are functionally distributed across many physical devices. In the case of virtual machines or hypervisors, all or part of a function may be provided in the form of software or firmware running over a virtualization layer to provide the disclosed logical function. In other examples, a device such as a network interface 260 may provide only the minimum hardware interfaces necessary to perform its logical operation, and may rely on a software driver to provide additional necessary logic. Thus, each logical block disclosed herein is broadly intended to include one or more logic elements configured and operable for providing the disclosed logical operation of that block. As used throughout this specification, "logic elements" may include hardware, external hardware (digital, analog, or mixed-signal), software, reciprocating software, services, drivers, interfaces, components, modules, algorithms, sensors, components, firmware, microcode, programmable logic, or objects that can coordinate to achieve a logical operation.

In an example, processor 210 is communicatively coupled to memory 220 via memory bus 270-3, which may be for example a direct memory access (DMA) bus by way of example, though other memory architectures are possible, including ones in which memory 220 communicates with processor 210 via system bus 270-1 or some other bus. Processor 210 may be communicatively coupled to other devices via a system bus 270-1. As used throughout this specification, a "bus" includes any wired or wireless interconnection line, network, connection, bundle, single bus, multiple buses, crossbar network, single-stage network, multistage network or other conduction medium operable to carry data, signals, or power between parts of a computing device, or between computing devices. It should be noted that these uses are disclosed by way of non-limiting example only, and that some embodiments may omit one or more of the foregoing buses, while others may employ additional or different buses.

In various examples, a "processor" may include any combination of logic elements operable to execute instructions, whether loaded from memory, or implemented directly in hardware, including by way of non-limiting example a microprocessor, digital signal processor, field-programmable gate array, graphics processing unit, programmable logic array, application-specific integrated circuit, or virtual machine processor. In certain architectures, a multi-core processor may be provided, in which case processor 210 may be treated as only one core of a multi-core processor, or may be treated as the entire multi-core processor, as appropriate. In some embodiments, one or more co-processor may also be provided for specialized or support functions.

Processor 210 may be connected to memory 220 in a DMA configuration via DMA bus 270-3. To simplify this disclosure, memory 220 is disclosed as a single logical block, but in a physical embodiment may include one or more blocks of any suitable volatile or non-volatile memory technology or technologies, including for example DDR RAM, SRAM, DRAM, cache, L1 or L2 memory, on-chip memory, registers, flash, ROM, optical media, virtual memory regions, magnetic or tape memory, or similar. In certain embodiments, memory 220 may comprise a relatively low-latency volatile main memory, while storage 250 may comprise a relatively higher-latency non-volatile memory. However, memory 220 and storage 250 need not be physically separate devices, and in some examples may represent simply a logical separation of function. It should also be noted that although DMA is disclosed by way of non-limiting example, DMA is not the only protocol consistent with this specification, and that other memory architectures are available.

Storage 250 may be any species of memory 220, or may be a separate device. Storage 250 may include one or more non-transitory computer-readable mediums, including by way of non-limiting example, a hard drive, solid-state drive, external storage, redundant array of independent disks (RAID), network-attached storage, optical storage, tape drive, backup system, cloud storage, or any combination of the foregoing. Storage 250 may be, or may include therein, a database or databases or data stored in other configurations, and may include a stored copy of operational software such as operating system 222 and software portions of verification engine 224. Many other configurations are also possible, and are intended to be encompassed within the broad scope of this specification.

Network interface 260 may be provided to communicatively couple client device 200 to a wired or wireless network. A "network," as used throughout this specification, may include any communicative platform operable to exchange data or information within or between computing devices, including by way of non-limiting example, an ad-hoc local network, an internet architecture providing computing devices with the ability to electronically interact, a plain old telephone system (POTS), which computing devices could use to perform transactions in which they may be assisted by human operators or in which they may manually key data into a telephone or other suitable electronic equipment, any packet data network (PDN) offering a communications interface or exchange between any two nodes in a system, or any local area network (LAN), metropolitan area network (MAN), wide area network (WAN), wireless local area network (WLAN), virtual private network (VPN), intranet, or any other appropriate architecture or system that facilitates communications in a network or telephonic environment.

Verification engine 224, in one example, is operable to carry out computer-implemented methods as described in this specification. Verification engine 224 may include one or more tangible non-transitory computer-readable mediums having stored thereon executable instructions operable to instruct a processor to provide a verification engine 224. As used throughout this specification, an "engine" includes any combination of one or more logic elements, of similar or dissimilar species, operable for and configured to perform one or more methods provided by the engine. Thus, verification engine 224 may comprise one or more logic elements configured to provide methods as disclosed in this specification. In some cases, verification engine 224 may include a special integrated circuit designed to carry out a method or a part thereof, and may also include software instructions operable to instruct a processor to perform the method. In some cases, verification engine 224 may run as a "daemon" process. A "daemon" may include any program or series of executable instructions, whether implemented in hardware, software, firmware, or any combination thereof that runs as a background process, a terminate-and-stay-resident program, a service, system extension, control panel, bootup procedure, BIOS subroutine, or any similar program that operates without direct user interaction. In certain embodiments, daemon processes may run with elevated privileges in a "driver space," or in ring 0, 1, or 2 in a protection ring architecture. It should also be noted that verification engine 224 may also include other hardware and software, including configuration files, registry entries, and interactive or user-mode software by way of non-limiting example.

In one example, verification engine 224 includes executable instructions stored on a non-transitory medium operable to perform a method according to this specification. At an appropriate time, such as upon booting client device 200 or upon a command from operating system 222 or a user 120, processor 210 may retrieve a copy of the instructions from storage 250 and load it into memory 220. Processor 210 may then iteratively execute the instructions of verification engine 224 to provide the desired method.

Figure 7:
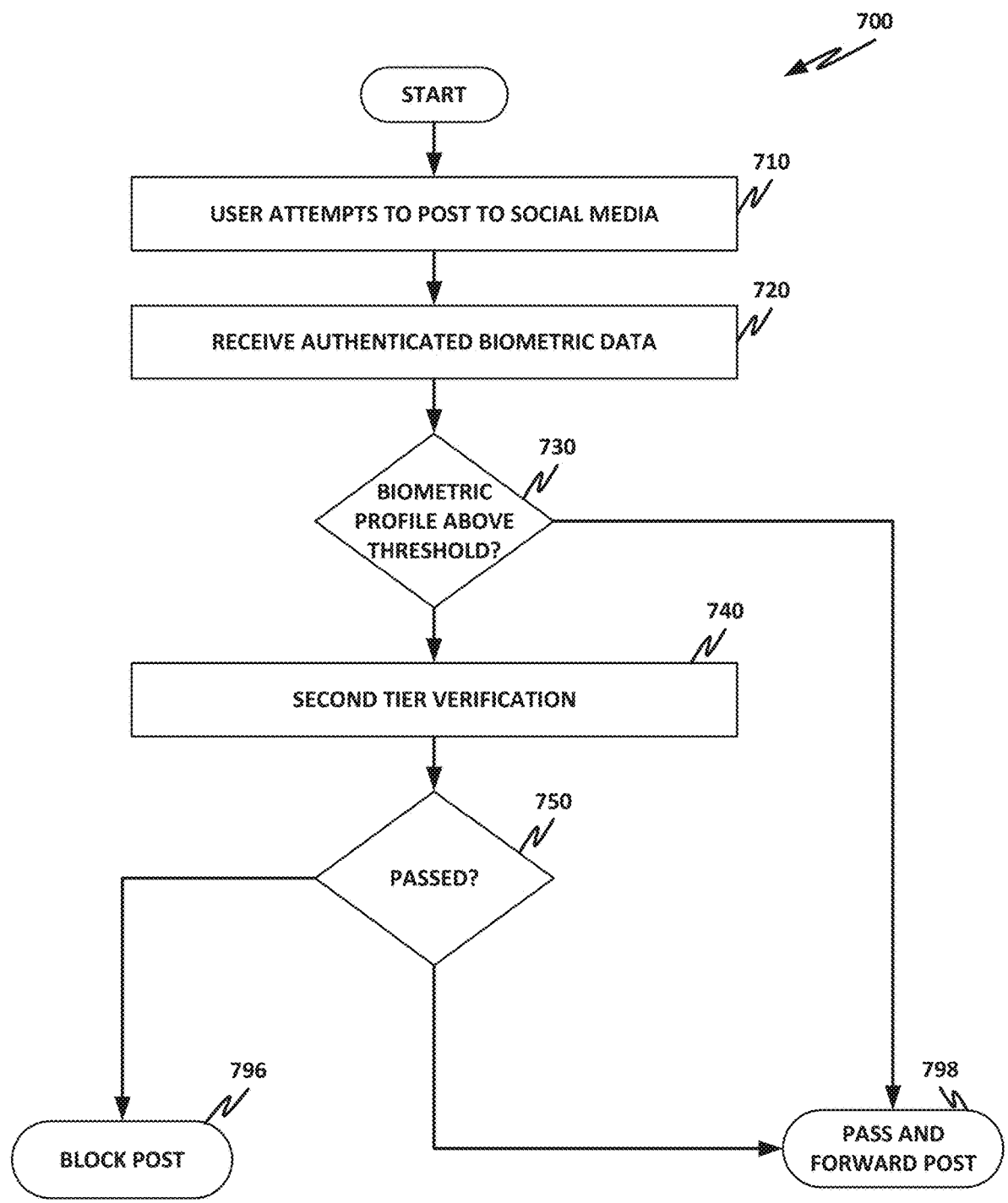
FIG. 7 is a flow chart of a method of a client device according to one or more examples of the present specification.

Verification engine 224 may be configured, in an embodiment, to carry out the method of FIG. 7, or other suitable methods of this specification. In this example, verification engine 224 operates on client device 110, but all or part may also operate on wearable device 130, or on any other suitable device.

Peripheral interface 240 may be configured to interface with any auxiliary device that connects to client device 200 but that is not necessarily a part of the core architecture of client device 200. A peripheral may be operable to provide extended functionality to client device 200, and may or may not be wholly dependent on client device 200. In some cases, a peripheral may be a computing device in its own right. Peripherals may include input and output devices such as displays, terminals, printers, keyboards, mice, modems, data ports (e.g., serial, parallel, USB, Firewire, or similar), network controllers, optical media, external storage, sensors, transducers, actuators, controllers, data acquisition buses, cameras, microphones, speakers, or external storage by way of non-limiting example.

In one example, peripherals include display adapter 242, audio driver 244, and input/output (I/O) driver 246. Display adapter 242 may be configured to provide a human-readable visual output, such as a command-line interface (CLI) or graphical desktop such as Microsoft Windows, Apple OSX desktop, or a Unix/Linux X Window System-based desktop. Display adapter 242 may provide output in any suitable format, such as a coaxial output, composite video, component video, VGA, or digital outputs such as DVI or HDMI, by way of nonlimiting example. In some examples, display adapter 242 may include a hardware graphics card, which may have its own memory and its own graphics processing unit (GPU). Audio driver 244 may provide an interface for audible sounds, and may include in some examples a hardware sound card. Sound output may be provided in analog (such as a 3.5 mm stereo jack), component ("RCA") stereo, or in a digital audio format such as S/PDIF, AES3, AES47, HDMI, USB, Bluetooth or Wi-Fi audio, by way of non-limiting example.

Figure 3:
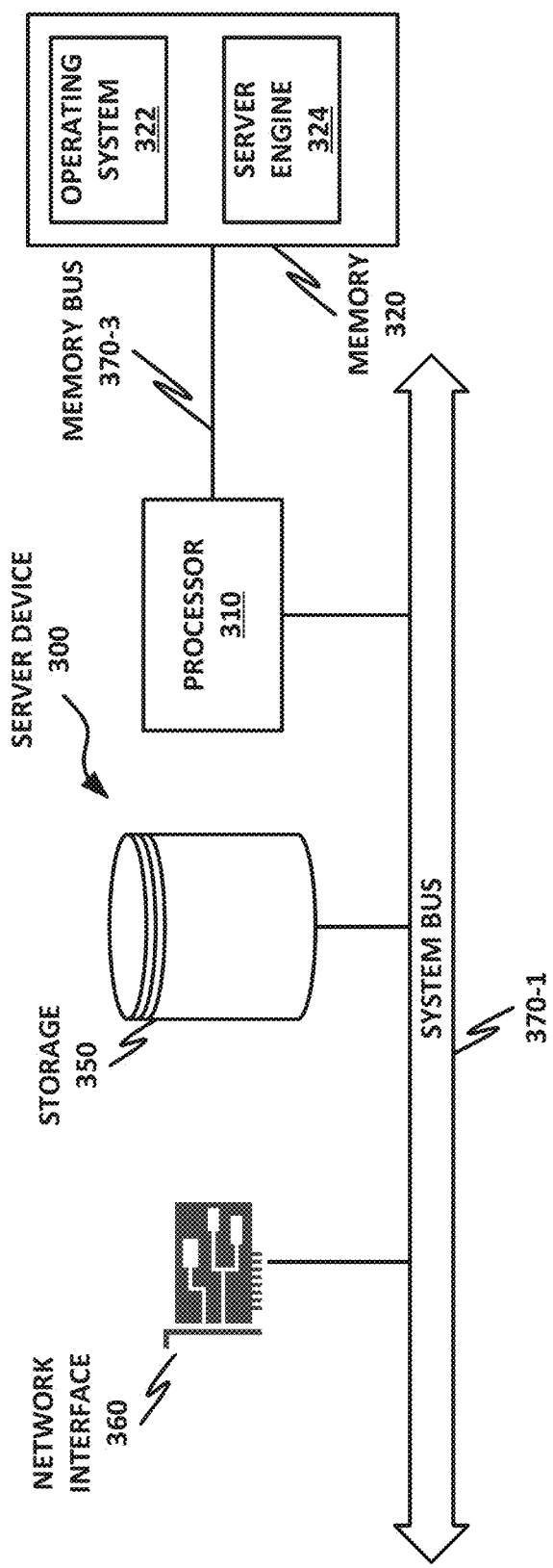
FIG. 3 is a block diagram of a server according to one or more examples of the present specification.

FIG. 3 is a block diagram of a server-class device 300 according to one or more examples of the present specification. Server 300 may be any suitable computing device, as described in connection with FIG. 2. In general, the definitions and examples of FIG. 2 may be considered as equally applicable to FIG. 3, unless specifically stated otherwise. Server 300 is described herein separately to illustrate that in certain embodiments, logical operations according to this specification may be divided along a client-server model, wherein client device 200 provides certain localized tasks, while server 300 provides certain other centralized tasks. In contemporary practice, server 300 is more likely than client device 200 to be provided as a "headless" VM running on a computing cluster, or as a standalone appliance, though these configurations are not required.

Server 300 includes a processor 310 connected to a memory 320, having stored therein executable instructions for providing an operating system 322 and at least software portions of a server engine 324. Other components of server 300 include a storage 350, and network interface 360. As described in FIG. 2, each logical block may be provided by one or more similar or dissimilar logic elements.

In an example, processor 310 is communicatively coupled to memory 320 via memory bus 370-3, which may be for example a direct memory access (DMA) bus. Processor 310 may be communicatively coupled to other devices via a system bus 370-1.

Processor 310 may be connected to memory 320 in a DMA configuration via DMA bus 370-3, or via any other suitable memory configuration. As discussed in FIG. 2, memory 320 may include one or more logic elements of any suitable type.

Storage 350 may be any species of memory 320, or may be a separate device, as described in connection with storage 250 of FIG. 2. Storage 350 may be, or may include therein, a database or databases or data stored in other configurations, and may include a stored copy of operational software such as operating system 322 and software portions of server engine 324.

Network interface 360 may be provided to communicatively couple server 140 to a wired or wireless network, and may include one or more logic elements as described in FIG. 2.

Server engine 324 is an engine as described in FIG. 2 and, in one example, includes one or more logic elements operable to carry out computer-implemented methods as described in this specification. Software portions of server engine 324 may run as a daemon process.

Server engine 324 may include one or more non-transitory computer-readable mediums having stored thereon executable instructions operable to instruct a processor to provide a security engine. At an appropriate time, such as upon booting server 140 or upon a command from operating system 322 or a user 120 or security administrator 150, processor 310 may retrieve a copy of server engine 324 (or software portions thereof) from storage 350 and load it into memory 320. Processor 310 may then iteratively execute the instructions of server engine 324 to provide the desired method.

Server engine 324 may be configured to provide a social media service, such as social media service 190. In some embodiments, server engine 324 may be explicitly configured to operate with end-to-end verification and encryption, in which case unverified inputs may be rejected.

Figure 4:
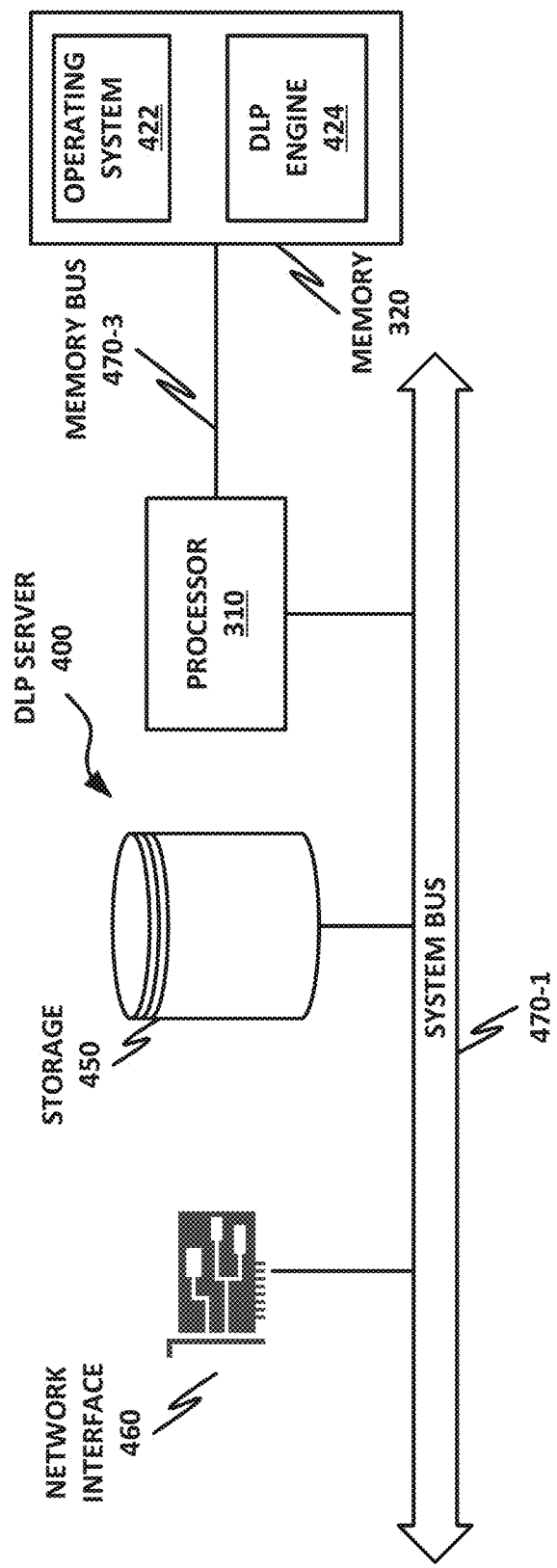
FIG. 4 is a block diagram of a data loss prevention (DLP) server according to one or more examples of the present specification.

FIG. 4 is a block diagram of a server-class device 400 according to one or more examples of the present specification. Server 400 may be any suitable computing device, as described in connection with FIG. 2. In general, the definitions and examples of FIG. 2 may be considered as equally applicable to FIG. 4, unless specifically stated otherwise. Server 400 is described herein separately to illustrate that in certain embodiments, logical operations according to this specification may be divided along a client-server model, wherein client device 200 provides certain localized tasks, while server 400 provides certain other centralized tasks. In contemporary practice, server 400 is more likely than client device 200 to be provided as a "headless" VM running on a computing cluster, or as a standalone appliance, though these configurations are not required.

Server 400 includes a processor 410 connected to a memory 420, having stored therein executable instructions for providing an operating system 422 and at least software portions of a DLP engine 424. Other components of server 400 include a storage 450, and network interface 460. As described in FIG. 2, each logical block may be provided by one or more similar or dissimilar logic elements.

In an example, processor 410 is communicatively coupled to memory 420 via memory bus 470-3, which may be for example a direct memory access (DMA) bus. Processor 410 may be communicatively coupled to other devices via a system bus 470-1.

Processor 410 may be connected to memory 420 in a DMA configuration via DMA bus 470-3, or via any other suitable memory configuration. As discussed in FIG. 2, memory 420 may include one or more logic elements of any suitable type.

Storage 450 may be any species of memory 420, or may be a separate device, as described in connection with storage 250 of FIG. 2. Storage 450 may be, or may include therein, a database or databases or data stored in other configurations, and may include a stored copy of operational software such as operating system 422 and software portions of DLP engine 424.

Network interface 460 may be provided to communicatively couple server 140 to a wired or wireless network, and may include one or more logic elements as described in FIG. 2.

DLP engine 424 is an engine as described in FIG. 2 and, in one example, includes one or more logic elements operable to carry out computer-implemented methods as described in this specification. Software portions of DLP engine 424 may run as a daemon process.

DLP engine 424 may include one or more non-transitory computer-readable mediums having stored thereon executable instructions operable to instruct a processor to provide a security engine. At an appropriate time, such as upon booting server 140 or upon a command from operating system 422 or a user 120 or security administrator 150, processor 410 may retrieve a copy of DLP engine 424 (or software portions thereof) from storage 450 and load it into memory 420. Processor 410 may then iteratively execute the instructions of DLP engine 424 to provide the desired method.

In some embodiments, DLP engine 424 may be provided separately on DLP server 400. However, it should be understood that some or all of the functions of DLP serer 400 may just as easily be provided on client device 110.

Figure 5:
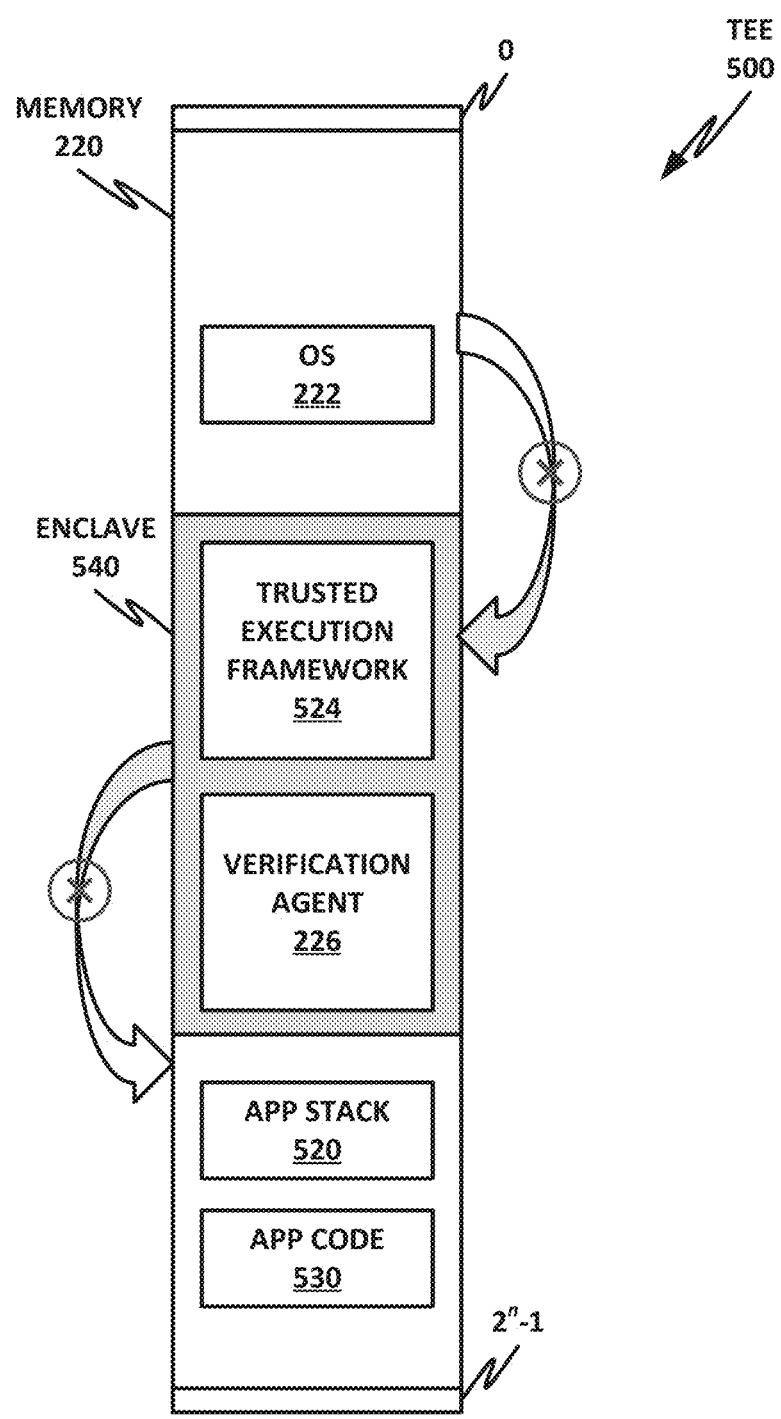
FIG. 5 is a block diagram of a trusted execution environment according to one or more examples of the present specification.

FIG. 5 is a block diagram of a trusted execution environment (TEE) 500 according to one or more examples of the present specification.

In the example of FIG. 5, memory 220 is addressable by n-bits, ranging in address from 0 to $2^n-1$. Within memory 220 is an OS 222, enclave 540, application stack 520, and application code 530.

In this example, enclave 540 is a specially-designated portion of memory 220 that cannot be entered into or exited from except via special instructions, such as Intel® SGX or similar. Enclave 540 is provided as an example of a secure environment which, in conjunction with a secure processing engine 510, forms a trusted execution environment (TEE) 500 on client device 200. A TEE 500 is a combination of hardware, software, and/or memory allocation that provides the ability to securely execute instructions without interference from outside processes, in a verifiable way. By way of example, TEE 500 may include memory enclave 540 or some other protected memory area, and a secure processing engine 510, which includes hardware, software, and instructions for accessing and operating on enclave 540. Non-limiting examples of solutions that either are or that can provide a TEE include Intel® SGX, ARM TrustZone, AMD Platform Security Processor, Kinibi, securiTEE, OP-TEE, TLK, T6, OpenTEE, and SierraTEE, CSE, VT-x, MemCore, Canary Island, Docker, and Smack. Thus, it should be noted that in an example, secure processing engine 510 may be a user-mode application that operates via trusted execution framework 524 within enclave 540. TEE 500 may also conceptually include processor instructions that secure processing engine 510 and trusted execution framework 524 require to operate within enclave 540.

Secure processing engine 510 and trusted execution framework 524 may together form a trusted computing base (TCB), which is a set of programs or computational units that are trusted to be secure. Conceptually, it may be advantageous to keep TCB relatively small so that there are fewer attack vectors for malware objects 182 or for negligent software. Thus, for example, operating system 222 may be excluded from TCB, in addition to the regular application stack 520 and application code 530.

In certain systems, computing devices equipped with the Intel Software Guard Extension (SGX) or equivalent instructions may be capable of providing an enclave 540. It should be noted however, that many other examples of TEEs are available, and TEE 500 is provided only as one example thereof. Other secure environments may include, by way of nonlimiting example, a virtual machine, sandbox, testbed, test machine, or other similar device or method for providing a TEE 500.

In an example, enclave 540 provides a protected memory area that cannot be accessed or manipulated by ordinary computer instructions. Enclave 540 is described with particular reference to an Intel® SGX enclave by way of example, but it is intended that enclave 540 encompass any secure processing area with suitable properties, regardless of whether it is called an "enclave."

One feature of an enclave is that once an enclave region 540 of memory 220 is defined, as illustrated, a program pointer cannot enter or exit enclave 540 without the use of special enclave instructions or directives, such as those provided by Intel® SGX architecture. For example, SGX processors provide the ENCLU[EENTER], ENCLU[ERESUME], and ENCLU[EEXIT]. These are the only instructions that may legitimately enter into or exit from enclave 540.

Thus, once enclave 540 is defined in memory 220, a program executing within enclave 540 may be safely verified to not operate outside of its bounds. This security feature means that secure processing engine 510 is verifiably local to enclave 540. Thus, when an untrusted packet provides its content to be rendered with trusted execution framework 524 of enclave 540, the result of the rendering is verified as secure.

Enclave 540 may also digitally sign its output, which provides a verifiable means of ensuring that content has not been tampered with or modified since being rendered by secure processing engine 510. A digital signature provided by enclave 540 is unique to enclave 540 and is unique to the hardware of the device hosting enclave 540.

Figure 6:
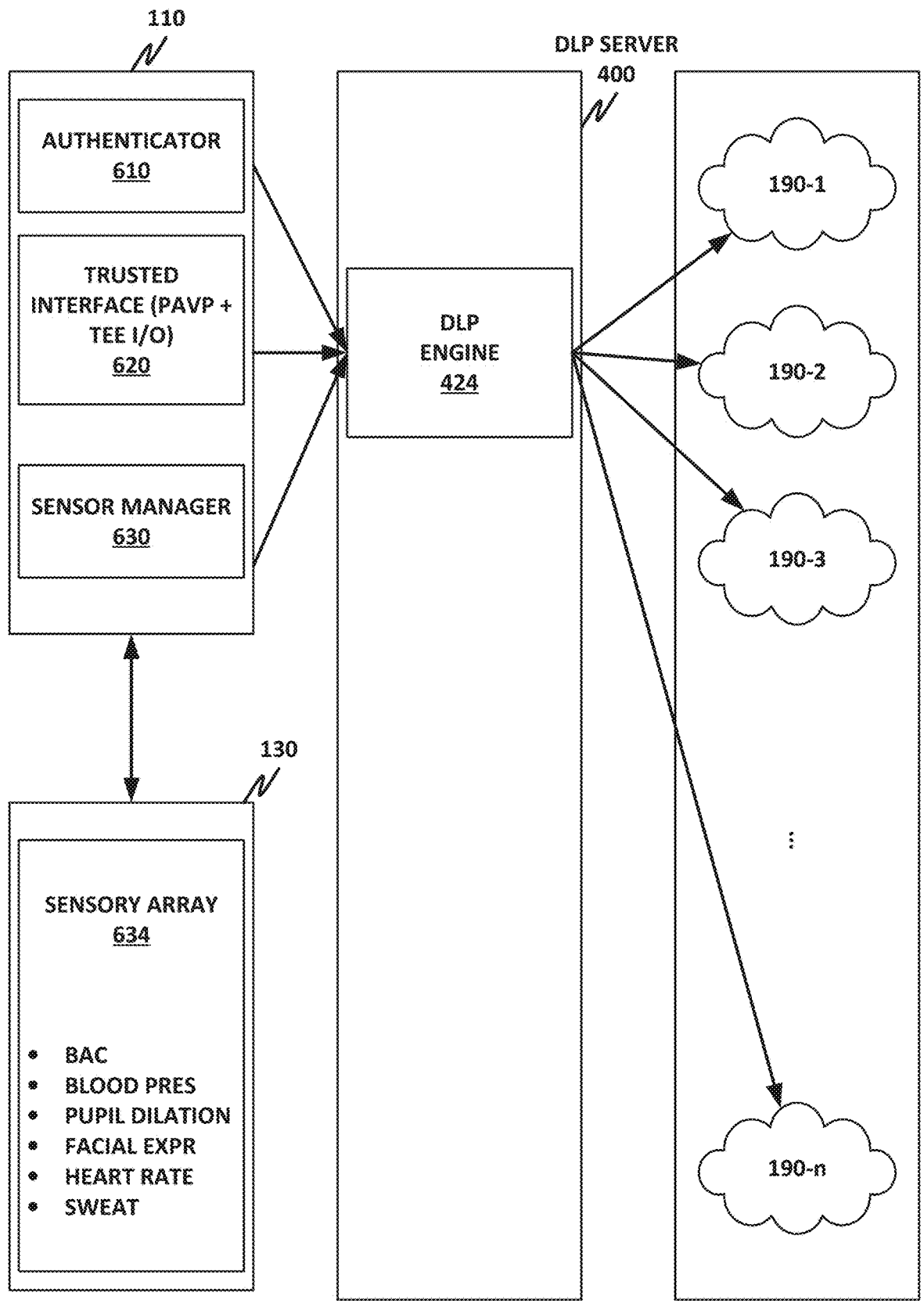
FIG. 6 is a block diagram of a verified social media content ecosystem according to one or more examples of the present specification.

FIG. 6 is a block diagram of a verified social media ecosystem according to one or more examples of the present specification. This ecosystem includes a client device 110, a wearable device 130, a DLP server 400, and one or more social media networks 190.

In this example, a user 120 operates a client device 110. Note that in accordance with the description provided in this specification, user 120 may be a corporate user, customer 162, or any other suitable user.

Client device 110 may be communicatively coupled to a wearable device 130. Client device 110 and wearable device 130 may together form the first line of defense against a user 120 making an inappropriate post to a social media site 190. Specifically, client device 110 includes, by way of example, an authenticator 610, trusted interface 620, and sensor manager 630.

Authenticator 610 may allow user 120 to authenticate by any suitable means, such as via a PIN, password, facial recognition, voice recognition, fingerprint, or any other suitable means. In an embodiment, the same biometric sensors of wearable device 130 may be used to provide initial user authentication. In other embodiments, different sensors may be provided, such as where dedicated biometric authentication sensors are used.

Trusted interface 620 may be the interface by which user 120 actually interoperates with a social media network. Trusted interface 620 may include a TEE, and also may include other security measures such as an Intel® protected audio-video path. This can be used to ensure that all peripherals 240, such as I/O devices, are protected. Memory 220 may also be protected via TEE 500.

Sensor manager 630 may be configured to securely communicatively couple to wearable device 130, and to engage in secured communications with wearable device 130. Measures such as trusted interface 620 and sensor manager 630 may help to ensure that client device 110 cannot be tampered with, such as to allow a user to post when not authorized.

As with client device 110, wearable device 130 may also include a TEE 500. Another important component of wearable device 130 is a sensor array 634. Sensor array 634 may include any suitable sensor to measure a user's ability, state of mind, or capacity to engage in an activity such as posting to a social media server. Nonlimiting examples of sensors in sensor array 634 include a blood alcohol content (BAC) sensor, blood pressure sensor, pupil dilation sensor, facial expression sensor, heart rate sensor, or perspiration sensor. These can all be used to help determine that a person is intoxicated, angry, nervous, or otherwise compromised to such an extent that he or she is not in full possession of faculties. Thus, it may be better for that user not to post to social network 190. Note that the biological profile may not, itself, directly implicate the user's ability to post. Rather, the biological profile may server as a proxy for, or a means to infer, a user's instantaneous psychological state. In a compromised psychological state, even if the user is mentally capable of composing a post and posting it, such a course may be ill-advised.

In an example, when a user 120 authenticates via authenticator 610, and then tries to operate trusted interface 620 to make a social media post, sensor manager 630 engages in a secured or attested communication with wearable device 130.

Attestation may be in the form of any suitable attestation, such as remote attestation, or "direct anonymous attestation" (DAA). In remote attestation, TEE 500 of wearable device 130 may generate a certificate of its hardware or software configuration. Wearable device 130 can present this certificate to client device 110 or DLP server 400 to prove that it has the required capability to securely measure biometric factors without tampering. This remote attestation may be combined with public-key encryption so that the information sent can only be read by the requesting device.

In certain embodiments, DAA may also be used to attest operations between wearable device 130 and client device 110, or more generally between any of the devices disclosed herein that perform attestation. In that case, the attesting device (here, wearable device 130, but in general, any of the devices disclosed herein that may perform attestation) may have a DAA certificate issued by a certificate authority, such as a public key infrastructure (PKI) certificate authority. The verifying device may be client device 110, or in general, any of the devices disclosed herein that may verify an attestation.

Each TEE 500 in the exchange includes an embedded RSA key pair called an Endorsement Key (EK), which the certificate authority is assumed to know. For attestation, TEE 500 of the attesting device (wearable device 130) generates a second RSA key pair called an Attestation Identity Key (AIK). It sends the public AIK, signed by EK, to the certificate authority, which checks its validity and issues a certificate for the AIK. The certificate authority may know the TEE's public EK a priori, or a device manufacturer may have provided an endorsement certificate. TEE 500 of wearable device 130 is now able to authenticate itself with respect to the certificate. Through a zero-knowledge proof engine, TEE 500 of the verifying device (client device 110) may verify the credential without attempting to violate the privacy of wearable device 130.

Upon a request from client device 110, wearable device 130 measures one or more suitable biometric parameters, and exchanges an encrypted packet with sensor manager 630. Sensor manager 630 then decrypts the packet, examines the data, and determines whether the biometric data are suitable for a post. Note that in some embodiments, more than one biometric datum may be used, in which case a biometric profile of user 120 may be built. The biometric profile may be a simple scalar score, or may be a multi-dimensional vector score with numerous factors. Verification engine 226 may compare this profile to either a scalar threshold, or to a multi-dimensional threshold vector, wherein each vector, or a minimum number of vectors, must exceed a threshold before a post is allowed.

In some cases, if user 120 fails the biometric profile, he may still be given an opportunity to post if he can pass a second-tier verification protocol, such as a suitable cognitive exercise. For example, the user may be asked to calculate a value such as his age multiplied by his dog's age. This exercise will be fairly simple for a sober person, but may be much more difficult for a person who is angry, intoxicated, or otherwise compromised. Second-tier content may also be based on personal knowledge not broadly known, thus providing an additional authentication factor. Other nonlimiting examples of verification exercises include forming a "word" from the first five letters of the user's first name and the first five letters of his mother's maiden name, sorting several cousins' names by order of age, finding a minimum number of objects in a "hidden picture" drawing, using a stylus or finger to navigate a maze or trace a pattern of straight lines, or solving a numerical or alphanumeric "captcha."

In some embodiments, verification engine 226 may be a standalone verification process. However, in other embodiments, it may be coupled with a DLP server 400, and/or a secured social media network 190.

In the case where verification engine 226 is not a standalone measure, verification engine 226 may sign the attempted social media content within TEE 500. Client device 110 may then provide the proposed content to DLP server 400.

DLP server 400 may receive the signed, encrypted post, and may in some cases perform an attestation with client device 110 to ensure that the content is genuine. DLP engine 424 may then decrypt the encrypted post and perform a natural-language scan of it, checking for content that may be against policy. DLP engine 424 may also scan multimedia files such as pictures, videos, or audio, using image or voice recognition to detect inappropriate content within those. Network administrator 150 may set suitable thresholds for how strictly which policies will be enforced. For example, there may be zero or near-zero tolerance for leakage of proprietary corporate data, while the criteria may be less stringent for something less important, such as appropriate fraternization at a corporate party. Other examples of problematic content may include personally-identifying information, insider trading, hate, or abuse.

DLP engine 424 may also, in certain embodiments, have responsibility for making decisions about the user's mental state. In those cases, client device 110 may not have logic for determining the user's state, but may rather simply provide a signed user state report, comprising raw or minimally-processed sensor data. DLP engine 424 may then determine whether the user is in condition to post, and may request a second-tier verification as appropriate. All transactions between DLP engine 424 and client device 110 may be securely encrypted and attested. In general, it should be understood that DLP engine 424 provides a verification function, but can be provided on DLP server 400, on client device 110, or on any other suitable device.

If DLP engine 424 determines that the post is appropriate, DLP engine 424 may sign the post (as necessary) and forward it to the target social media network 190.

In some embodiments, social media network 190 may be a secured social media network, in which case it may only accept signed content submissions, or it may favor or otherwise perform special classification for signed content. In some embodiments, social media network 190 may be equipped with servers that have TEE capabilities so that it can perform remote attestation with DLP engine 424 or with client device 110.

Note that while popular networks with a large and diverse user base are less likely to strictly enforce a secure computing model, there are examples of networks where secure computing can be advantageous. For example, a government agency, intelligence agency, or defense agency may wish to provide its own internal social network to further its enterprise purposes. In that case, it may be advantageous to require secure connections. And even large networks with diverse user bases may provide secure connection as a user option, so that users can help to secure their accounts from compromise, either from a third party, or from their own inadvertent errors.

Advantageously, at a top level, the ecosystem of FIG. 6 may provide a completely secure, end-to-end encrypted and attested means for interacting with a social network, with every connection from wearable device 130 to social media network 190 secured, attested, and/or encrypted. In that case, an attestation chain may include wearable device 130→client device 110→DLP server 400→social media server 190.

In appropriate circumstances, attestation may take other forms than ensuring that data are not compromised. For example, attestation may be used between client device 110 and wearable device 130 to ensure that wearable device 130 has the minimum hardware and software capabilities to provide the desired biometric input.

FIG. 7 is a flow chart of a method 700 performed by a client device 110 according to one or more examples of the present specification.

In block 710, a user 120 attempts to take a requested user action that is subject to verification, such as posting to a social media network, accessing sensitive data, or any other action that may be subject to control of a verification engine 226 or DLP engine 424. Any such action may be referred to herein as a "controlled action." This action is referred to as a "post" by way of nonlimiting example.

In block 730, client device 110 may receive biometric data from wearable device 130. Additional details of such an exchange in an example are disclosed above. These data may be received via a secured communication channel, such as via a TEE 500 or by other suitable means. The data may be encrypted, and attestation between client device 110 and wearable device 130 may be performed as appropriate, for example as discussed above.

In block 730, verification engine 226 determines whether a biometric profile is above a threshold. For example, this may include ensuring that the user's BAC does not exceed a specified value, that the user's pulse or perspiration are not above a specified value, or any other suitable input for inferring user 120's state of mind. As discussed above, the biometric profile may be a single scalar or normalized composite value, or it may be a multi-dimensional vector value. Thus, determining whether the biometric profile is above a value may comprise either comparing the single scalar value to a threshold, or comparing a plurality of values to a plurality of thresholds. The result of this comparing may be a binary indication that the user's profile has either "passed" or "failed."

If the user passes, then in block 798, the post has passed verification. In an embodiment, once verification engine 226 has passed the post, verification engine 226 forwards the post, which may include forwarding the post to social media service 190 in an embodiment where no separate DLP engine 424 is provided, or may include forwarding the post, along with a signed user state report, to separate DLP engine 424.

If the user fails the biometric profile check, he may be provided with a second opportunity to take his action. For example, the user may receive a second-tier verification request, which in an embodiment is a cognitive activity that will be more difficult to perform while compromised. This may include any of the example activities disclosed above, or any other suitable activity.

Figure 8:
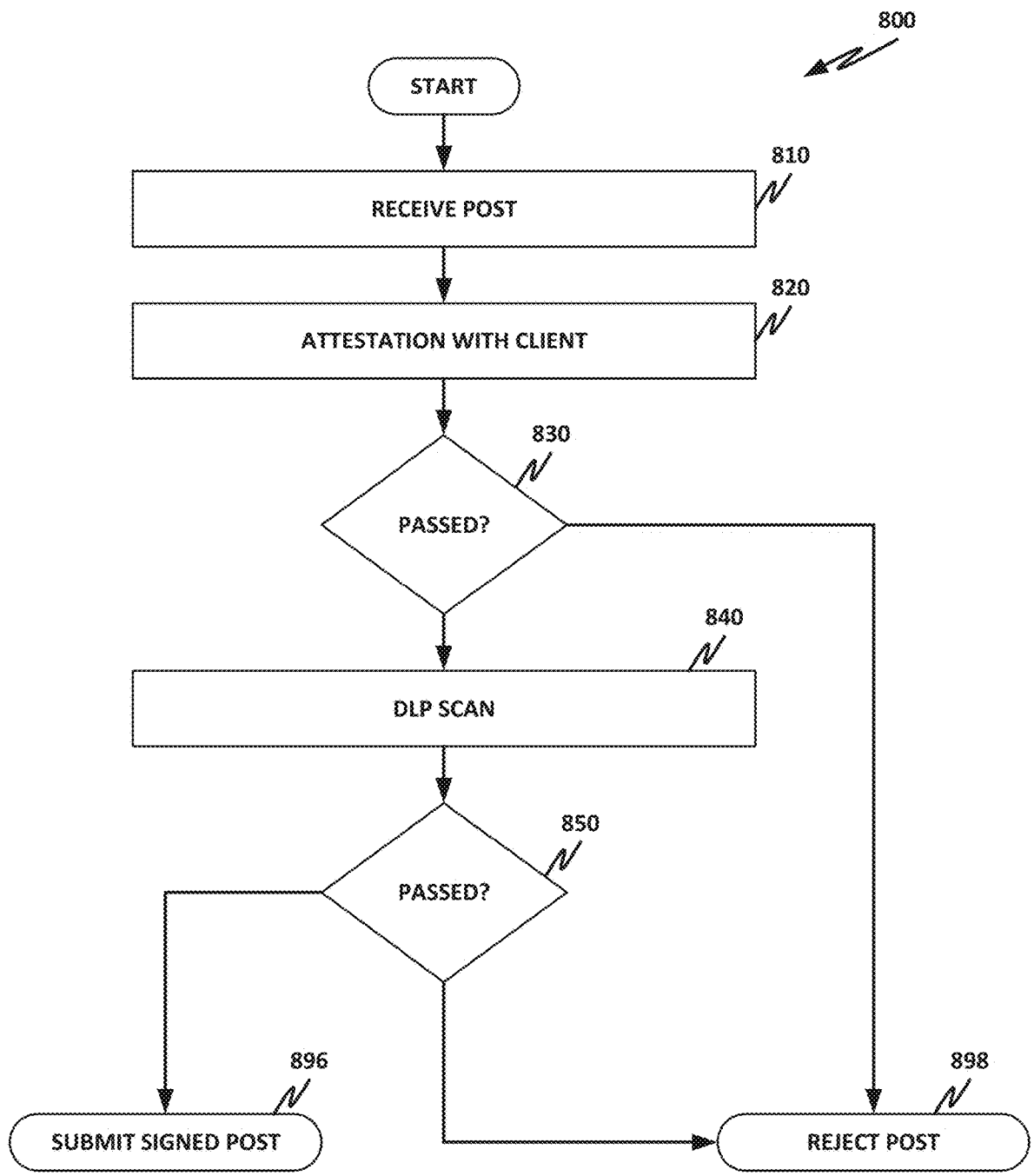
FIG. 8 is a flow chart of a method of a DLP server according to one or more examples of the present specification.

FIG. 8 is a flow chart of a method 800 performed by DLP engine 424 according to one or more examples of the present specification.

In block 810, DLP engine 424 receives an attempted post or other requested user action from client device 110. Note that this may be received via a network interface and TEE. For example, this may include a signed user state report as above.

In block 820, DLP engine 424 performs an attestation with client 110 to ensure that authenticity of the attempted post. Attestation is discussed in additional detail above.

In decision block 830, if the attestation fails, then in block 898, the post is rejected. However, if the attestation is successful, in block 840, DLP engine 424 performs a DLP scan on the attempted post. "DLP" in the context of the specification is intended to be construed very broadly to encompass any factor that may make the post inappropriate. Examples of checks that may be performed in a DLP scan are discussed above.

In block 850, if the post fails DLP inspection, then in block 898, the post is rejected. As discussed above, a post may be rejected, by way of nonlimiting example, for malicious or hateful content, proprietary corporate data, government classified data, personally-identifying information, insider trading, content or statements against policy, personal opinions put forth as official corporate policy or without appropriate disclaimers, or other inappropriate content.

If the post passes DLP inspection, then in block 896, DLP engine 424 submits the post to a social media network 190. Note that in some cases, the post is signed with the TEE so that end-to-end encryption and verification can be provided, from wearable device 130 to social media network 190. As appropriate, attestations may be performed as discussed in additional detail above.

Note that the methods of FIG. 7 and FIG. 8 are disclosed as two separate methods, one performed by client device and one performed by DLP server 400. But it should be understood that this division is provided by way of nonlimiting example only. In appropriate circumstances, any of the operations may be suitably combined. For example, DLP server 400 may instead simply be a DLP engine running on client device 110, with no centralized server. In other embodiments, client device 110 may only collect biometric inputs and provide a TEE and PAVP connection to DLP engine 424, in which case all decisions (e.g., blocks 730 forward in FIG. 7) may be made on DLP server 400.

Figure 9:
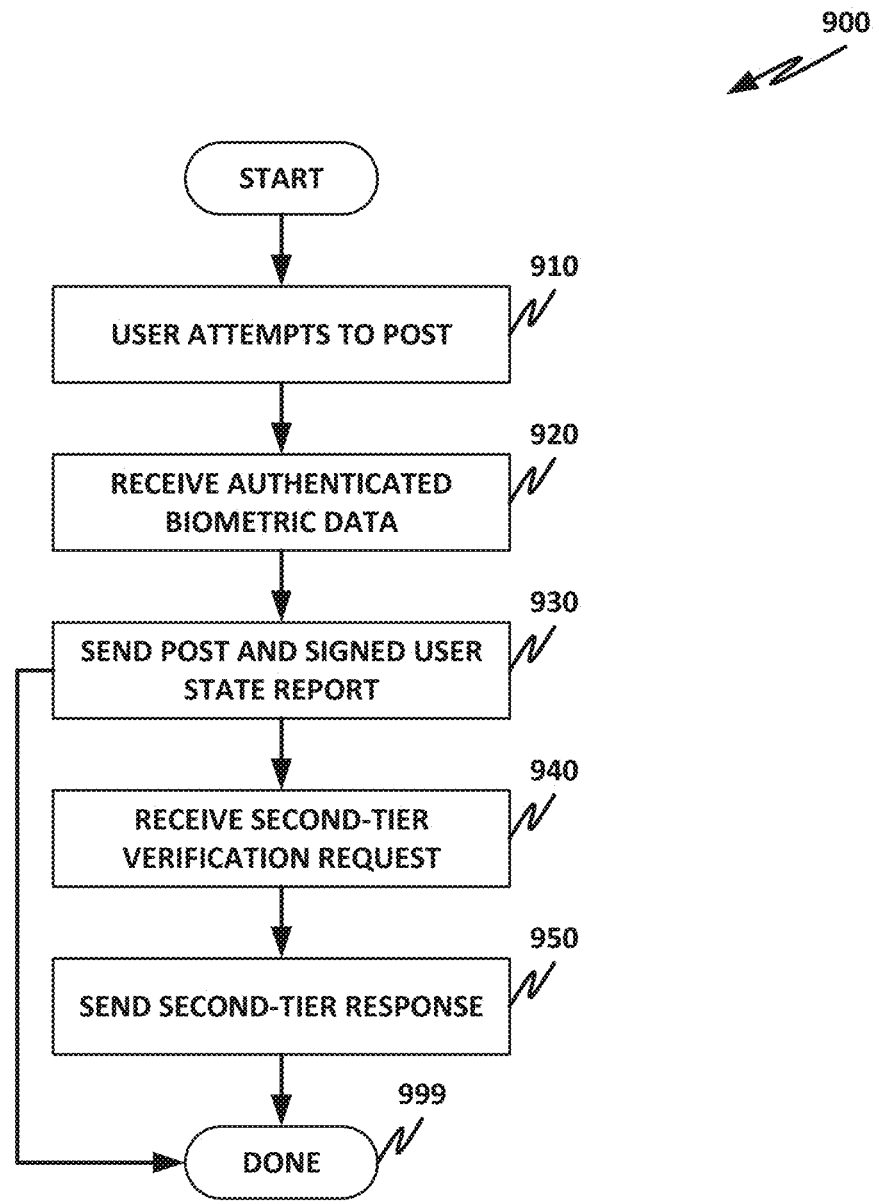
FIG. 9 is a flow chart of a method performed by a client device according to one or more examples of the present specification.
Figure 10:
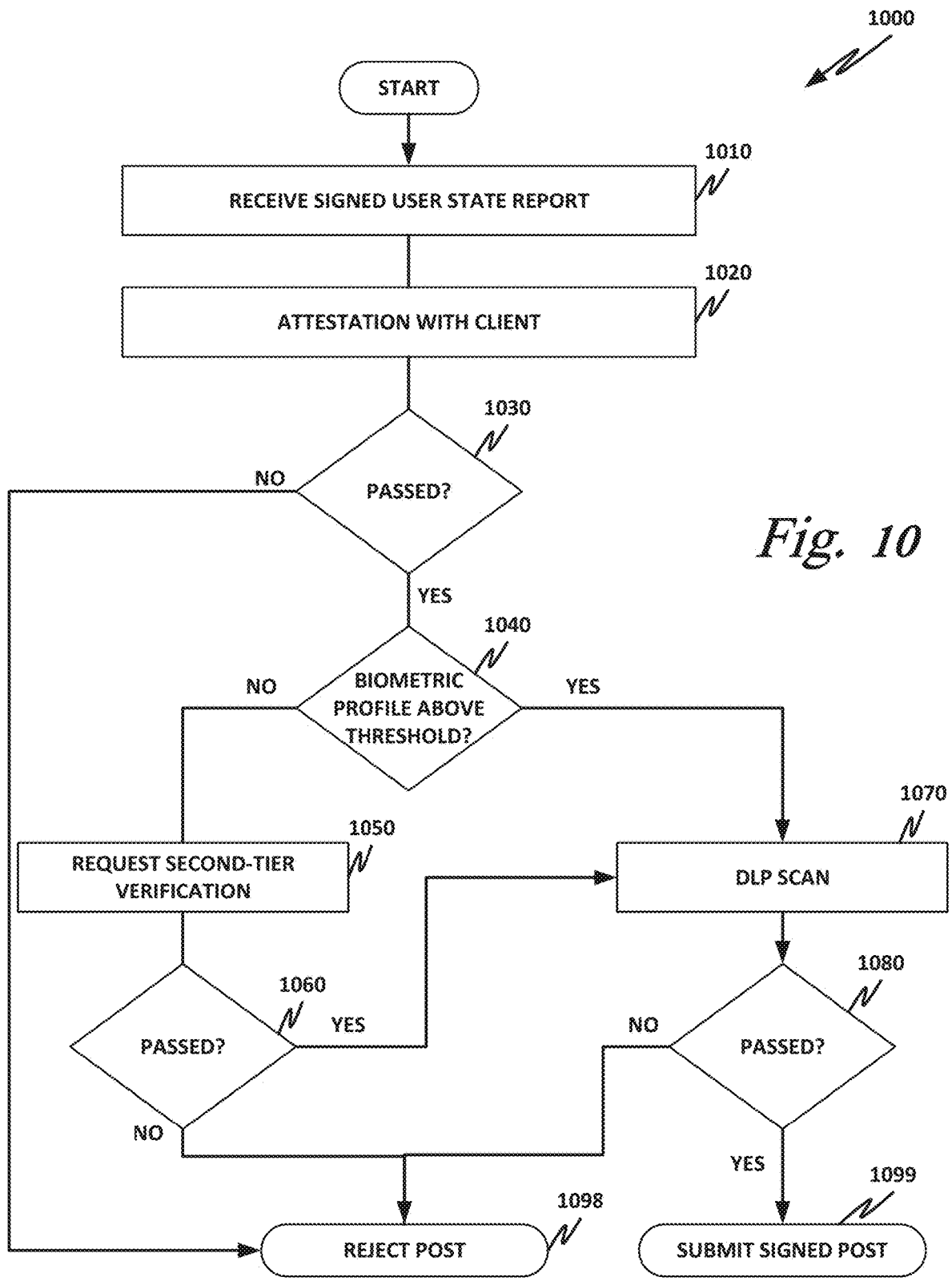
FIG. 10 is a flow chart of a method performed by a DLP server according to one or more examples of the present specification.

FIGS. 9 and 10 are flow charts of methods performed by client device 110 and DLP server 400 in such an example, where client device 110 performs only minimal processing.

Method 900 of FIG. 9 is performed by client device 110.

In block 910, a user attempts to take a controller user action that is subject to verification, (see above). This action is referred to as a "post" by way of nonlimiting example.

In block 920, client device 110 may receive biometric data from wearable device 130. Additional details of such an exchange in an example are disclosed above. These data may be received via a secured communication channel, such as via a TEE 500 or by other suitable means. The data may be encrypted, and attestation between client device 110 and wearable device 130 may be performed as appropriate, for example as discussed above.

In block 930, client device 110 sends the attempted post (or other data, as appropriate to the embedment), along with a signed user state report to DLP server 400. Additional details of constructing a signed user state report are discussed above. Note that in this embodiment, verification engine 226 may have performed no or minimal processing on the signed user state report.

In the absence of further communication from DLP server 400, method 900 is done at block 999.

However, in some cases, verification engine 226 may receive from DLP server 400 a second-tier verification request. This may indicate that the user's biometric profile did not pass scrutiny by DLP server 400. Examples of second-tier verification requests are provided above.

In block 950, verification engine 226 presents the second-tier verification challenge to user 120, for example via trusted interface 620. The user of trusted interface 620 can help to ensure that there has been no tampering, such as the user preparing macros of correct responses to known tests. The user provides an appropriate input, and in some embodiments, verification engine 226 may score the result. In another embodiment, verification engine 226 may simply send the user's signed and attested input to DLP server 400 for scoring.

In block 999, method 900 is done.

FIG. 10 is a flow chart of method 1000 performed by DLP engine 424 of DLP server 400, in conjunction with client device 110 performing method 900 of FIG. 9.

In block 1010, DLP engine 424 receives from client device 110 a signed user state report, for example the one that client device 110 sent in block 930 of FIG. 9.

In block 1020, DLP engine 424 may perform an attestation with client device 110. Attestation is described in more detail above.

In decision block 1030, DLP engine 424 determines whether the attestation was successful. If not, then in block 1098, DLP engine 424 rejects the post.

If the attestation is successful, then in decision block 1040, DLP engine 424 determines whether the user's biometric profile is above a threshold. For example, this may include ensuring that the user's BAC does not exceed a specified value, that the user's pulse or perspiration are not above a specified value, or any other suitable input for inferring user 120's state of mind. As discussed above, the biometric profile may be a single scalar or normalized composite value, or it may be a multi-dimensional vector value. Thus, determining whether the biometric profile is above a value may comprise either comparing the single scalar value to a threshold, or comparing a plurality of values to a plurality of thresholds. The result of this comparing may be a binary indication that the user's profile has either "passed" or "failed."

If the user fails the biometric profile check, then in block 1050, DLP engine 424 may request a second-tier verification from client device 110. Examples of second-tier verification exercises are provided above. In response, DLP engine 424 may either receive raw user input, or it may receive a scored second-tier verification report from client device 110.

In decision block 1060, if the user fails the second-tier verification, then in block 1098, DLP engine 424 rejects the post or other attempted action.

If the user either passes the biometric profile check in block 1040, or passes the second tier verification in block 1060, then in block 1070, DLP engine 424 performs a DLP scan on the attempted post or other action. Examples of DLP scans are discussed above.

In decision block 1080, DLP engine 424 determines whether the post has passed the DLP scan. If not, then in block 1098, DLP engine 424 rejects the post.

In block 1099, if the post passes the DLP scan, then DLP engine 424 424 submits the post to a social media network 190. Note that in some cases, the post is signed with the TEE so that end-to-end encryption and verification can be provided, from wearable device 130 to social media network 190. As appropriate, attestations may be performed as discussed in additional detail above.

Note that in combination, FIGS. 7 and 8 and FIGS. 9 and 10 respectively disclose two examples of dividing biometric verification from DLP analysis. In the example of FIGS. 7 and 8, biometric verification is performed on client device 110, while DLP scanning is performed on DLP server 400 or alternatively on client device 110. In the embodiment of FIGS. 9 and 10, client device 110 provides only unprocessed or minimally processed inputs to DLP server 400. These two examples should be understood to be nonlimiting examples. In a general sense, any embodiment may divide responsibilities between DLP server 400 and client device 110 as the demands of the particular embodiment demand. DLP server 400 could also be provided on, or in conjunction with, a social media server 190, or in any other appropriate configuration.

The foregoing outlines features of several embodiments so that those skilled in the art may better understand various aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

All or part of any hardware element disclosed herein may readily be provided in a system-on-a-chip (SoC), including central processing unit (CPU) package. An SoC represents an integrated circuit (IC) that integrates components of a computer or other electronic system into a single chip. Thus, for example, client devices 110 or server devices 300 may be provided, in whole or in part, in an SoC. The SoC may contain digital, analog, mixed-signal, and radio frequency functions, all of which may be provided on a single chip substrate. Other embodiments may include a multi-chip-module (MCM), with a plurality of chips located within a single electronic package and configured to interact closely with each other through the electronic package. In various other embodiments, the computing functionalities disclosed herein may be implemented in one or more silicon cores in Application Specific Integrated Circuits (ASICs), Field Programmable Gate Arrays (FPGAs), and other semiconductor chips.

Note also that in certain embodiment, some of the components may be omitted or consolidated. In a general sense, the arrangements depicted in the figures may be more logical in their representations, whereas a physical architecture may include various permutations, combinations, and/or hybrids of these elements. It is imperative to note that countless possible design configurations can be used to achieve the operational objectives outlined herein. Accordingly, the associated infrastructure has a myriad of substitute arrangements, design choices, device possibilities, hardware configurations, software implementations, and equipment options.

In a general sense, any suitably-configured processor, such as processor 210, can execute any type of instructions associated with the data to achieve the operations detailed herein. Any processor disclosed herein could transform an element or an article (for example, data) from one state or thing to another state or thing. In another example, some activities outlined herein may be implemented with fixed logic or programmable logic (for example, software and/or computer instructions executed by a processor) and the elements identified herein could be some type of a programmable processor, programmable digital logic (for example, a field programmable gate array (FPGA), an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machine-readable mediums suitable for storing electronic instructions, or any suitable combination thereof.

In operation, a storage such as storage 250 may store information in any suitable type of tangible, non-transitory storage medium (for example, random access memory (RAM), read only memory (ROM), field programmable gate array (FPGA), erasable programmable read only memory (EPROM), electrically erasable programmable ROM (EEPROM), etc.), software, hardware (for example, processor instructions or microcode), or in any other suitable component, device, element, or object where appropriate and based on particular needs. Furthermore, the information being tracked, sent, received, or stored in a processor could be provided in any database, register, table, cache, queue, control list, or storage structure, based on particular needs and implementations, all of which could be referenced in any suitable timeframe. Any of the memory or storage elements disclosed herein, such as memory 220 and storage 250, should be construed as being encompassed within the broad terms 'memory' and 'storage,' as appropriate. A non-transitory storage medium herein is expressly intended to include any non-transitory special-purpose or programmable hardware configured to provide the disclosed operations, or to cause a processor such as processor 210 to perform the disclosed operations.

Computer program logic implementing all or part of the functionality described herein is embodied in various forms, including, but in no way limited to, a source code form, a computer executable form, machine instructions or microcode, programmable hardware, and various intermediate forms (for example, forms generated by an assembler, compiler, linker, or locator). In an example, source code includes a series of computer program instructions implemented in various programming languages, such as an object code, an assembly language, or a high-level language such as OpenCL, FORTRAN, C, C++, JAVA, or HTML for use with various operating systems or operating environments, or in hardware description languages such as Spice, Verilog, and VHDL. The source code may define and use various data structures and communication messages. The source code may be in a computer executable form (e.g., via an interpreter), or the source code may be converted (e.g., via a translator, assembler, or compiler) into a computer executable form, or converted to an intermediate form such as byte code. Where appropriate, any of the foregoing may be used to build or describe appropriate discrete or integrated circuits, whether sequential, combinatorial, state machines, or otherwise.

In one example embodiment, any number of electrical circuits of the FIGURES may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processor and memory can be suitably coupled to the board based on particular configuration needs, processing demands, and computing designs. Other components such as external storage, additional sensors, controllers for audio/video display, and peripheral devices may be attached to the board as plug-in cards, via cables, or integrated into the board itself. In another example, the electrical circuits of the FIGURES may be implemented as stand-alone modules (e.g., a device with associated components and circuitry configured to perform a specific application or function) or implemented as plug-in modules into application specific hardware of electronic devices.

Note that with the numerous examples provided herein, interaction may be described in terms of two, three, four, or more electrical components. However, this has been done for purposes of clarity and example only. It should be appreciated that the system can be consolidated or reconfigured in any suitable manner. Along similar design alternatives, any of the illustrated components, modules, and elements of the FIGURES may be combined in various possible configurations, all of which are within the broad scope of this specification. In certain cases, it may be easier to describe one or more of the functionalities of a given set of flows by only referencing a limited number of electrical elements. It should be appreciated that the electrical circuits of the FIGURES and its teachings are readily scalable and can accommodate a large number of components, as well as more complicated/sophisticated arrangements and configurations. Accordingly, the examples provided should not limit the scope or inhibit the broad teachings of the electrical circuits as potentially applied to a myriad of other architectures.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 112 (pre-AIA) or paragraph (f) of the same section (post-AIA), as it exists on the date of the filing hereof unless the words "means for" or "steps for" are specifically used in the particular claims; and (b) does not intend, by any statement in the specification, to limit this disclosure in any way that is not otherwise expressly reflected in the appended claims.

EXAMPLE IMPLEMENTATIONS

There is disclosed in one example, a social media server, comprising: a processor; a trusted input/output (IO) interface to communicatively couple to a consumer device; a network interface to communicatively couple to an enterprise; and a memory having stored thereon executable instructions to instruct the processor to provide a data loss prevention (DLP) engine to: receive via the trusted IO interface a signed and encrypted user posting for the social media service, the user posting including a signed user state report verifying that the user has passed a biometric screening; transmit content of the user posting to the enterprise via the network interface for DLP analysis; receive from the enterprise a notification that the user posting has passed DLP analysis; and accept the user posting.

There is further disclosed an example social media server, wherein the DLP engine is further to receive from the enterprise a notification that the user posting has failed DLP analysis and to reject the user posting.

There is further disclosed an example social media server, wherein the DLP engine is further to determine that the user posting does not include a signed user state report, and to reject the user posting.

There is further disclosed an example social media server, wherein the trusted IO interface includes a protected audio video path (PAVP).

There is further disclosed an example social media server, further comprising a trusted execution environment (TEE).

There is further disclosed an example social media server, wherein the DLP engine is further to perform direct anonymous attestation (DAA) with the user device to authenticate the user device.

There is further disclosed an example social media server, wherein the DAA comprises an exchange of endorsement keys.

There is further disclosed an example social media server, wherein the TEE comprises a zero-knowledge proof engine to authenticate the user device without compromising privacy of the user device.

There are also disclosed in an example, one or more tangible, non-transitory computer-readable storage mediums having stored thereon executable instructions to provide a data loss prevention (DLP) engine configured to: receive via a trusted input/output (IO) channel a secured user posting for a social media service, the user posting including a user state report verifying that the user meets a minimum biometric profile; transmit content of the user posting to an enterprise for DLP analysis; receive from the enterprise a notification that the user posting has passed DLP analysis; and accept the user posting.

There are further disclosed in an example, one or more tangible, non-transitory computer-readable mediums, wherein the DLP engine is further configured to receive from the enterprise a notification that the user posting has failed DLP analysis and to reject the user posting.

There are further disclosed in an example, one or more tangible, non-transitory computer-readable mediums, wherein the DLP engine is further configured to determine that the user posting does not include a signed user state report, and to reject the user posting.

There are further disclosed in an example, one or more tangible, non-transitory computer-readable mediums, wherein the trusted IO channel includes a protected audio video path (PAVP).

There are further disclosed in an example, one or more tangible, non-transitory computer-readable mediums, wherein the instructions are further to provision a trusted execution environment (TEE).

There are further disclosed in an example, one or more tangible, non-transitory computer-readable mediums wherein the DLP engine is further configured to perform direct anonymous attestation (DAA) with a user device to authenticate the user device.

There are further disclosed in an example, one or more tangible, non-transitory computer-readable mediums wherein the DAA comprises an exchange of endorsement keys.

There are further disclosed in an example, one or more tangible, non-transitory computer-readable mediums wherein the TEE comprises a zero-knowledge proof engine to authenticate the user device without compromising privacy of a user providing the posting.

There is also disclosed in an example, a computer-implemented method of providing enterprise data loss prevention (DLP) for a social media service, comprising: receiving via a trusted input/output (IO) path a posting for the social media service, the user posting accompanied by a state report verifying that the user has passed a non-authentication biometric screening; extracting content from the posting; transmitting the content to an enterprise for DLP analysis; receiving from the enterprise a certification that the user posting has passed DLP analysis; and providing the user posting to the social media service.

There is further disclosed in an example, a method further comprising receiving from the enterprise a notification that the user posting has failed DLP analysis and to reject the user posting.

There is further disclosed in an example, a method further comprising determining that the user posting does not include a state report, and to reject the user posting.

There is further disclosed in an example, a method wherein the state report is signed and encrypted.

There is further disclosed in an example, a method wherein the trusted IO channel includes a protected audio video path (PAVP).

There is further disclosed in an example, a method further comprising providing a trusted execution environment (TEE).

There is further disclosed in an example, a method further comprising performing direct anonymous attestation (DAA) with a user device to authenticate the user device.

There is further disclosed in an example, a method wherein the DAA comprises an exchange of endorsement keys.

There is further disclosed in an example, a method wherein the TEE comprises a zero-knowledge proof engine to authenticate the user device without compromising privacy of a user providing the posting.

What is claimed is:

1. A social media server, comprising:
    a processor;
    a trusted input/output (IO) interface to communicatively couple to a consumer device;
    a network interface to communicatively couple to an enterprise; and
    a memory having stored thereon executable instructions to instruct the processor to provide a data loss prevention (DLP) engine to:
        receive via the trusted IO interface a signed and encrypted user posting for the social media service, the user posting including a signed user state report verifying that the user has passed a biometric screening;
        transmit content of the user posting to the enterprise via the network interface for DLP analysis;
        receive from the enterprise a notification that the user posting has passed DLP analysis; and
        accept the user posting.

2. The social media server of claim 1, wherein the DLP engine is further to receive from the enterprise a notification that the user posting has failed DLP analysis and to reject the user posting.

3. The social media server of claim 1, wherein the DLP engine is further to determine that the user posting does not include a signed user state report, and to reject the user posting.

4. The social media server of claim 1, wherein the trusted IO interface includes a protected audio video path (PAVP).

5. The social media server of claim 1, further comprising a trusted execution environment (TEE).

6. The social media server of claim 5, wherein the DLP engine is further to perform direct anonymous attestation (DAA) with the user device to authenticate the user device.

7. The social media server of claim 6, wherein the DAA comprises an exchange of endorsement keys.

8. The social media server of claim 7, wherein the TEE comprises a zero-knowledge proof engine to authenticate the user device without compromising privacy of the user device.

9. One or more tangible, non-transitory computer-readable storage mediums having stored thereon executable instructions to provide a data loss prevention (DLP) engine configured to:
    receive via a trusted input/output (IO) channel a secured user posting for a social media service, the user posting including a user state report verifying that the user meets a minimum biometric profile;
    transmit content of the user posting to an enterprise for DLP analysis;
    receive from the enterprise a notification that the user posting has passed DLP analysis; and
    accept the user posting.

10. The one or more tangible, non-transitory computer-readable mediums of claim 9, wherein the DLP engine is further configured to receive from the enterprise a notification that the user posting has failed DLP analysis and to reject the user posting.

11. The one or more tangible, non-transitory computer-readable mediums of claim 9, wherein the DLP engine is further configured to determine that the user posting does not include a signed user state report, and to reject the user posting.

12. The one or more tangible, non-transitory computer-readable mediums of claim 9, wherein the trusted IO channel includes a protected audio video path (PAVP).

13. The one or more tangible, non-transitory computer-readable mediums of claim 9, wherein the instructions are further to provision a trusted execution environment (TEE).

14. The one or more tangible, non-transitory computer-readable mediums of claim 13, wherein the DLP engine is further configured to perform direct anonymous attestation (DAA) with a user device to authenticate the user device.

15. The one or more tangible, non-transitory computer-readable mediums of claim 14, wherein the DAA comprises an exchange of endorsement keys.

16. The one or more tangible, non-transitory computer-readable mediums of claim 13, wherein the TEE comprises a zero-knowledge proof engine to authenticate the user device without compromising privacy of a user providing the posting.

17. A computer-implemented method of providing enterprise data loss prevention (DLP) for a social media service, comprising:

receiving via a trusted input/output (IO) path a posting for the social media service, the user posting accompanied by a state report verifying that the user has passed a non-authentication biometric screening;

extracting content from the posting;

transmitting the content to an enterprise for DLP analysis;

receiving from the enterprise a certification that the user posting has passed DLP analysis; and providing the user posting to the social media service.

18. The method of claim 17, further comprising receiving from the enterprise a notification that the user posting has failed DLP analysis and to reject the user posting.

19. The method of claim 17, further comprising determining that the user posting does not include a state report, and to reject the user posting.

20. The method of claim 19, wherein the state report is signed and encrypted.

* * * * *